United States Patent [19]

Russell

[11] Patent Number: 4,786,731

[45] Date of Patent: Nov. 22, 1988

[54] RESOLUTION OF ENANTIOMERS OF 2-(PHENYL OR PHENOXY)PROPIONIC ACIDS USING OPTICALLY ACTIVE ALKANOLAMINES

[75] Inventor: John W. Russell, Midland, Mich.

[73] Assignee: The Dow Chemical Company, Midland, Mich.

[21] Appl. No.: 81,519

[22] Filed: Aug. 5, 1987

[51] Int. Cl.$^4$ .................. C07D 241/36; C07D 211/72; C07B 57/00
[52] U.S. Cl. .................................... 544/354; 546/295; 71/92; 71/94; 71/109; 71/116; 560/21; 560/45; 560/59; 560/61; 560/56; 560/62; 560/100; 560/102; 560/105; 562/401; 562/402; 562/469; 562/472
[58] Field of Search ............... 562/401, 402, 435, 452, 562/456, 457, 466, 469, 471, 472, 490, 492, 496; 560/21, 45, 59, 61, 62, 56, 100, 102, 105; 544/354; 546/295

[56] References Cited

U.S. PATENT DOCUMENTS

| | | | |
|---|---|---|---|
| 3,954,442 | 5/1976 | Becker et al. | 71/108 |
| 4,332,960 | 6/1982 | Trosken et al. | 560/62 |
| 4,531,969 | 7/1985 | Nestler et al. | 71/108 |
| 4,550,192 | 10/1985 | Rogers et al. | 560/62 |

OTHER PUBLICATIONS

Souter, *Chromatographic Separations of Stereoiomers*, CRC Press, Boca Raton, Fla., pp. 68-69, (1985).

*Primary Examiner*—Werren B. Lone
*Assistant Examiner*—Vera C. Clarke
*Attorney, Agent, or Firm*—Craig E. Mixan; Ronald G. Brookens

[57] ABSTRACT

A method for the chromatographic resolution and analysis of the enantiomers of 2-(phenyl or phenoxy)propionic acids or the $C_1$–$C_4$ alkyl esters thereof which comprises converting a racemic or partially resolved mixture of said 2-(phenyl or phenoxy)propionic acids or the $C_1$–$C_4$ alkyl esters thereof to a pair of diastereomeric 2-amino-1-alkanol derivatives by reaction with an optically active 2-amino-1-alkanol, and analyzing the diastereomeric mixture by gas chromatography.

6 Claims, No Drawings

RESOLUTION OF ENANTIOMERS OF 2-(PHENYL OR PHENOXY)PROPIONIC ACIDS USING OPTICALLY ACTIVE ALKANOLAMINES

BACKGROUND OF THE INVENTION

The herbicidal activity of 2-(4-aryloxyphenoxy)propionic acids and derivatives thereof is well known in the art. Furthermore, optical isomers are often known to exhibit enhanced herbicidal activity over the corresponding racemates. For example, U.S. Pat. No. 4,531,969 discloses that the R-enantiomers of certain 2-(4-aryloxyphenoxy)propionic acids and certain derivatives thereof are distinguished by a considerably enhanced herbicidal action compared to the racemic modifications. Since reduced quantities of herbicide are required to achieve comparable levels of control, the application of mixtures enriched in the more efficacious R-enantiomer offers both economical and environmental advantages. Analogous advantages exist in the pharmaceutical art as exemplified by the anti-inflammatory 2-(phenyl)propionic acids such as ibuprofen.

In order to commercially exploit the benefits of the advantages associated with the use of the biologically more active enantiomer, it is necessary to accurately determine the ratio of the R- and S-enantiomers in a specific composition. Besides allowing one to monitor the production process, such analytical capability is required to support product labeling and registration requirements. One of the most versatile methods of achieving such an analysis involves the synthesis of diastereomeric derivatives. By reacting a racemate or a partially resolved mixture of enantiomers with an optically active reagent, a pair of diastereomeric derivatives are produced which can be separated on the basis of their different physical properties.

For carboxylic acids in general, including the 2-(phenyl or phenoxy)propionic acids, optically active amines such as α-methyl benzyl amine have found widespread use as the resolving agents of choice. Oftentimes, however, the chromatographic separations of the pair of diastereomers is less than ideal. Furthermore, quantification is not always accurate because of the purity of the commercial samples available or because of slight racemization during the derivatization reaction. This proves particularly troublesome where accurate determinations of relatively small amounts of one diastereomer in the presence of relatively large amounts of the other are desired.

SUMMARY OF THE INVENTION

The present invention provides a method for the chromatographic resolution and analysis of the enantiomers of 2-(phenyl or phenoxy)propionic acids of formula I

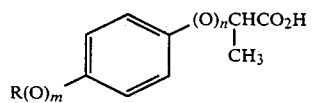

wherein R and H, $C_1-C_4$ alkyl or Ar, m and n are independently 0 or 1,
and Ar is an unsubstituted or substituted phenyl or heterocyclic ring system
or the $C_1-C_4$ alkyl esters thereof which comprises converting a racemic or partially resolved mixture of said 2-(phenyl or phenoxy)propionic acid or $C_1-C_4$ alkyl ester thereof to a pair of diastereomeric 2-amino-1-alkanol derivatives by reaction with an optically active 2-amino-1-alkanol, and analyzing the diastereomeric mixture by gas chromatography.

The 2-(4-aryloxyphenoxy)propionic acids and lower alkyl esters thereof to which the present method may be applied are disclosed for example in U.S. Pat. Nos. 3,954,442, 4,332,960, 4,370,489, 4,531,969, 4,550,192, 4,565,568, 4,600,432 and 4,609,396 and in European patent applications publication Nos. 0000483 and 0001473.

Particularly valuable examples of 2-(4-aryloxyphenoxy)propionic acids to which the present method may be applied are of formula:

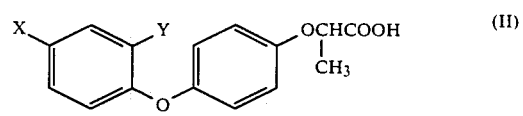

wherein X is $CF_3$, F, Cl, Br, I, CN, $NO_2$ or $NH_2$ and Y is H, F, Cl, Br or I,

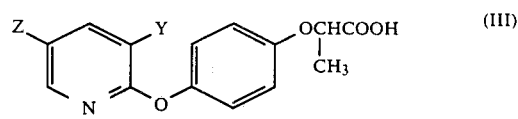

wherein Z is $CF_3$, F, Cl, Br or I and Y is as defined above, and

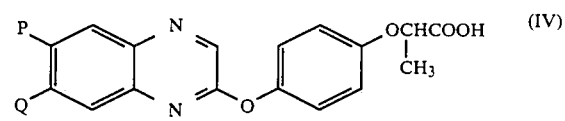

wherein P and Q are independently H, F, Cl, Br or I.

For compounds of formula II, X is preferably Cl, Br, I or CN and Y is preferably F or Cl.

For compounds of formula III, Z is preferably $CF_3$, Cl, Br or I and Y is preferably H, F or Cl.

For compounds of formula IV, one of P or Q is preferably F or Cl.

Besides providing a useful method for analyzing the enantiomeric composition of 2-(4-aryloxyphenoxy)propionic acids and esters themselves, the present invention is also useful for analyzing 2-(4-alkoxyphenoxy)propionic acids and esters thereof including 2-(4-hydroxyphenoxy)propionic acid. Such 2-(4-alkoxyphenoxy)propionic acids and esters are known to be useful intermediates for the preparation of 2-(4-aryloxyphenoxy)propionate herbicides.

The present invention is also useful for analyzing 2-(4-alkylphenyl)propionic acids and esters thereof, such as, for example, ibuprofen which is an anti-inflammatory drug.

Although any optically active 2-amino-1-alkanol is contemplated as the resolving agent, those derived from naturally occurring α-amino acids, such as, for example, alaninol and phenylalaninol, are preferred. Commercially available D- or L-alaninol, i.e., R-(−)- or S-(+)-2-amino-1-propanol, are the most preferred reagents.

The diastereomeric 2-amino-1-alkanol derivatives can be prepared by a variety of techniques, either with or without a solvent. It is important that the chosen procedure avoids racemization of the chiral center which leads to subsequent error in the analysis. Both D-alaninol and L-alaninol are apparently less prone to racemization than is α-methyl benzyl amine under analogous reaction conditions. Furthermore, unlike α-methyl benzyl amine, the alaninols can be reacted directly with esters of 2-(4-aryloxyphenoxy)propionates under mild conditions.

Appropriate procedures include, for example, the treatment of the racemic or partially resolved 2-(4-alkyl or aryl)oxyphenoxy)propionic acid with excess thionyl chloride to form the acid chloride. Removal of the excess thionyl chloride followed by reaction of the acid chloride with an optically active 2-amino-1-alkanol, for example D-alaninol or L-alaninol, provides a product consisting of a pair of diastereomeric derivatives.

Alternatively, the $C_1$–$C_4$ alkyl esters of the 2-(phenyl or phenoxy)propionic acids can be directly reacted with an excess of an optically active 2-amino-1-alkanol at elevated temperature. The excess 2-amino-1-alkanol need not be removed since it does not interfere with the subsequent analysis.

With D- or L-alaninol, the diastereomeric derivatives produced are hydroxyalkyl amides vis. the N-(2-hydroxy-1-methylethyl)propionamides.

The pair of diastereomeric hydroxyalkyl amides obtained as described herein can be separated and analyzed by gas chromatography. The effectiveness of a particular chromatographic separation is subject to several variables that are well appreciated by those skilled in the art. In general, the accuracy achieved using optically active 2-amino-1-alkanols as the resolving agents is superior to that obtained using optically active amines such as α-methyl benzyl amine. As a result, the method of the present invention allows for a more accurate and precise determination of optical purity in samples containing a preponderance of one enantiomer over the other.

DETAILED DESCRIPTION OF THE INVENTION

The following examples illustrate the invention:

EXAMPLE 1

A sample (2 mg) of racemic methyl 2-(4-((3-chloro-5-trifluoromethyl-2-pyridinyl)oxy)phenoxy)propionate was reacted directly with 25 mg of L-alaninol in a 1 mL reaction vial for 30 minutes at 55° C. (~70 percent conversion). After cooling, 0.8 mL of methylene chloride were added and 2 μL injected into a capillary gas chromatograph using the following conditions:
Column:
  12 m×0.20 mm ID, 0.33μ film cross-linked methyl silicone (Hewlett-Packard)
Temperatures:
Injection Port—250° C.
Column—120° C. to 260° C. at 16° C./min
Flame Ionization Detector—280° C.
Helium Flow Rates:
Column—150 kPa, 67 cm/sec
Split—100 mL/min The area percent analysis of the racemic sample gave an R/S ratio of 50.1/49.9.

EXAMPLE 2

A partially resolved sample of methyl 2-(4-((3-chloro-5-trifluoromethyl-2-pyridinyl)oxy)phenoxy)propionate containing 91 percent R-enantiomer and 9 percent S-enantiomer as determined by nuclear magnetic resonance spectroscopy employing an optically active shift reagent was treated and analyzed according to the procedure of Example 1. The area percent analysis gave an R/S ratio of 91.0/9.0.

EXAMPLE 3

A highly purified sample of methyl 2-(4-((3-fluoro-5-trifluoromethyl-2-pyridinyl)oxy)phenoxy)propionate containing 99.8 percent R-enantiomer and 0.2 percent S-enantiomer as determined by nuclear magnetic resonance was treated according to the procedure of Example 1. The area percent analysis gave an R/S ratio of 99.8/0.2.

EXAMPLE 4

Synthetic mixtures of partially resolved methyl 2-(4-((3-fluoro-5-trifluoromethyl-2-pyridinyl)oxy)phenoxy)-propionate were generated by combining accurately weighed amounts of the corresponding resolved sample having an R/S ratio of 99.4/0.6 and a racemic mixture and melting together at 100° C. until mixed. In some cases methylene chloride was added to afford mixing. Samples were prepared and analyzed according to the procedures of Example 1. The results are summarized in Table I.

TABLE I

Determination of Enantiomer Ratios of Synthetic Methyl 2-(4-((3-fluoro-5-trifluoromethyl-2-pyridinyl)oxy)-phenoxy)propionate Samples Using L-Alaninol

| Sample | Known R/S | Determined R/S |
|---|---|---|
| A | 50.00/50.00 | 49.93/50.07 |
| B | 84.36/15.64 | 84.36/15.64 |
| C | 91.61/8.39 | 91.74/8.26 |
| D | 93.72/6.28 | 93.73/6.27 |
| E | 95.31/4.69 | 95.29/4.71 |
| F | 96.37/3.63 | 96.31/3.69 |
| G | 98.41/1.59 | 98.33/1.67 |

EXAMPLE 5

Racemic mixtures of the compounds in Table II were derivatized by reacting 2–3 mg in a 1 mL Reacti-Vial with 40 mg L-alaninol (L-2-amino-1-propanol, Sigma) for 1 hour at 70° C. After cooling, 0.7 mL methylene chloride were added and 0.5 μL injected into the capillary GC.
GC Conditions:
Column:
  12 m×0.20 mm ID, 0.33μ film cross-linked methyl silicone
Temperatures
Inj. Port: 250° C.
Column: 120° C. to 260° C. at 16°/min.
FID: 280° C.
He Flows
Septum Purge: 3 mL/min.
Column: 150 kPa, 67 cm/sec.
Split: 100 mL/min.
Attenuation: $4 \times 10^{-11}$ The 2-(phenyl)propionic acid esters 1 and 2 did not react as methyl esters directly with the reagent. Therefore, the free acids of 1 and 2 were reacted by adding 40 mg of thionyl chloride to 3 mg and heating at 70° C. until evaporation of all of the thionyl chloride. Then 40 mg of l-alaninol were added and heated 10 minutes at 70° C. After cooling, 0.7 mL methylene chloride were added.

GC Conditions:
Column:
  12 m×0.20 mm ID, 0.33μ film cross-linked methyl silicone
Temperatures
Inj. Port: 250° C.
Column: 120° C. to 260° C. at 12°/min.
FID: 280° C.
He Flows
Septum Purge: 3 mL/min.
Column: 100 kPa
Split: 100 mL/min.
Attenuation: $4 \times 10^{-11}$ The retention times of the diastereomers are reported in Table II. In each instance, the R/S ratio was within the range of 0.992 and 1.008.

TABLE II

Resolution of Racemates with L-alaninol

| | Compound | Retention Time (minutes) |
|---|---|---|
| 1. | C6H5-CH(CH3)-CO-OCH3 | 5.08/5.19 |
| 2. | (CH3)2CHCH2-C6H4-CH(CH3)-CO-OCH3 | 7.92/8.03 |
| 3. | HO-C6H4-O-CH(CH3)-CO-OCH3 | 7.08/7.22 |
| 4. | CH3O-C6H4-O-CH(CH3)-CO-OCH3 | 6.39/6.57 |
| 5. | CN-C6H3(F)-O-C6H4-O-CH(CH3)-CO-OCH3 | 10.73/10.90 |
| 6. | NH2-C6H3(Cl)-O-C6H4-O-CH(CH3)-CO-OCH3 | 13.78/14.07 |
| 7. | NO2-C6H3(Cl)-O-C6H4-O-CH(CH3)-CO-OCH3 | 15.01/15.37 |
| 8. | NO2-C6H3(F)-O-C6H4-O-CH(CH3)-CO-OCH3 | 12.15/12.37 |
| 9. | Br-C6H3(Cl)-O-C6H4-O-CH(CH3)-CO-OCH3 | 12.56/12.80 |

TABLE II-continued
Resolution of Racemates with L-alaninol

| | Compound | Retention Time (minutes) |
|---|---|---|
| 10. | 4-iodo-2-fluorophenyl — O — phenyl — OCH(CH₃)COCH₃ | 11.94/12.13 |
| 11. | 4-chloro-2-chlorophenyl — O — phenyl — OCH(CH₃)COCH₃ | 11.27/11.45 |
| 12. | 4-chloro-2-fluorophenyl — O — phenyl — OCH(CH₃)COCH₃ | 9.73/9.85 |
| 13. | 4-bromo-2-fluorophenyl — O — phenyl — OCH(CH₃)COCH₃ | 10.89/11.05 |
| 14. | 5-CF₃-pyridin-2-yl — O — phenyl — OCH(CH₃)COCH₃ | 8.53/8.68 |
| 15. | 5-CF₃-3-chloro-pyridin-2-yl — O — phenyl — OCH(CH₃)COCH₃ | 9.20/9.36 |
| 16. | 5-CF₃-3-fluoro-pyridin-2-yl — O — phenyl — OCH(CH₃)COCH₃ | 8.19/8.33 |
| 17. | 7-chloroquinoxalin-2-yl — O — phenyl — OCH(CH₃)COCH₃ | 17.10/17.69 |

Various modifications may be made in the present invention without departing from the spirit or scope thereof, and it is understood that I limit myself only as defined in the appended claims.

I claim:

1. A method for the chromatographic resolution and analysis of the enantiomers of 2-(4-(alkyl or aryl)oxyphenoxy)propionic acids of the formula

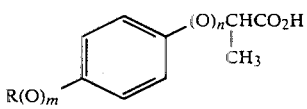

wherein R is H, C₁–C₄ alkyl or Ar, m and n are independently 0 or 1, and Ar is an unsubstituted or substituted phenyl pyridinyl or quinoxalinyl ring system or the C₁–C₄ alkyl esters thereof which comprises converting a racemic or partially resolved mixture of said 2-(4-(alkyl or aryl)oxyphenoxy)propionic acid or $C_1$–$C_4$ alkyl ester thereof to a pair of diastereomeric 2-amino-1-alkanol derivatives by reaction with an optically active 2-amino-1-alkanol under conditions that avoid racemization and analyzing the diastereomeric mixture by gas chromatography.

2. The method of claim 1 in which the optically active 2-amino-1-alkanol is D-2-amino-1-propanol or L-2-amino-1-propanol.

3. The method of claim 2 in which the 2-(4-(alkyl or aryl)oxyphenoxy)propionic acid is of the formula

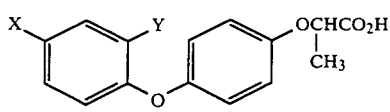

wherein X is $CF_3$, F, Cl, Br, I, CN, $NH_2$ or $NO_2$ and Y is H, F, Cl, Br or I or the $C_1$–$C_4$ alkyl esters thereof.

4. The method of claim 2 in which the 2-(4-alkyl or aryloxyphenoxy)propionic acid is of the formula

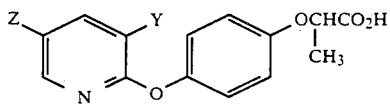

wherein Z is $CF_3$, F, Cl, Br or I and Y is H, F, Cl, Br or I or the $C_1$–$C_4$ alkyl esters thereof.

5. The method of claim 2 in which the 2-(4-(phenyl or phenoxy)propionic acid is of the formula

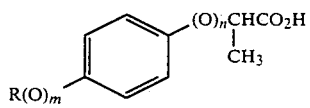

wherein R is H or $C_1$–$C_4$ alkyl and m and n are independently 0 or 1 or the $C_1$–$C_4$ alkyl esters thereof.

6. The method of claim 2 in which the 2-(4-(alkyl or aryl)oxyphenoxy)propionic acid is of the formula

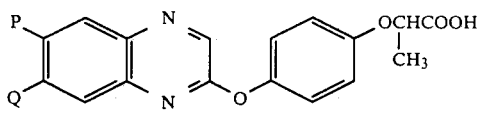

wherein P and Q are independently H, F, Cl, Br or I.

* * * * *